US012668360B2

(12) United States Patent
Wang et al.

(10) Patent No.: US 12,668,360 B2
(45) Date of Patent: Jun. 30, 2026

(54) IN-SITU DETECTION DEVICE AND METHOD FOR CARBON EMISSIONS FROM FARMLAND

(71) Applicant: Zhejiang University, Hangzhou City (CN)

(72) Inventors: Yueying Wang, Hangzhou City (CN); Yong He, Hangzhou City (CN); Liwen He, Hangzhou City (CN)

(73) Assignee: Zhejiang University, Hangzhou City (CN)

( * ) Notice: Subject to any disclaimer, the term of this patent is extended or adjusted under 35 U.S.C. 154(b) by 0 days.

(21) Appl. No.: 19/072,069

(22) Filed: Mar. 6, 2025

(65) Prior Publication Data

US 2025/0282478 A1 Sep. 11, 2025

(30) Foreign Application Priority Data

Mar. 11, 2024 (CN) .......................... 202410268859.4

(51) Int. Cl.
| | |
|---|---|
| *B64D 1/00* | (2006.01) |
| *B64U 10/13* | (2023.01) |
| *B64U 60/30* | (2023.01) |
| *B64U 101/40* | (2023.01) |
| *G01N 33/00* | (2006.01) |

(52) U.S. Cl.
CPC .............. *B64D 1/00* (2013.01); *B64U 10/13* (2023.01); *B64U 60/30* (2023.01); *G01N 33/0036* (2013.01); *B64U 2101/40* (2023.01)

(58) Field of Classification Search
None
See application file for complete search history.

(56) References Cited

U.S. PATENT DOCUMENTS

2022/0041282 A1 * 2/2022 Oren ...................... B01D 53/04

FOREIGN PATENT DOCUMENTS

| | | | | | |
|---|---|---|---|---|---|
| CN | 117388434 A | * | 1/2024 | ............. | B64U 20/80 |
| CN | 117848790 A | * | 4/2024 | ............. | G01D 21/02 |
| CN | 118833432 A | * | 10/2024 | ............. | G01S 15/08 |
| CN | 119240022 A | * | 1/2025 | ......... | G01N 33/0009 |
| EP | 4481370 A1 | * | 12/2024 | ............. | G01N 21/39 |

* cited by examiner

*Primary Examiner* — Richard G Davis
(74) *Attorney, Agent, or Firm* — Tutunjian & Bitetto, P.C.

(57) ABSTRACT

Provided are an in-situ detection device and method for carbon emissions from farmland. The in-situ detection device includes an unmanned aerial vehicle, and landing gear. A retraction and release mechanism is arranged between the unmanned aerial vehicle and the landing gear, and the retraction and release mechanism is configured for retracting or lowering the landing gear. An enrichment hood is installed on the landing gear through a folding mechanism, and the folding mechanism can drive the enrichment hood to be unfolded or folded on the landing gear. When the unmanned aerial vehicle lowers the landing gear to a farmland gas collection point through the retraction and release mechanism, the enrichment hood is unfolded to enrich a gas at the farmland gas collection point. The landing gear is also provided with a greenhouse gas detection mechanism for detecting the gas enriched in the enrichment hood.

13 Claims, 3 Drawing Sheets

IN-SITU DETECTION DEVICE AND METHOD FOR CARBON EMISSIONS FROM FARMLAND

CROSS-REFERENCE TO RELATED APPLICATION

This patent application claims the benefit and priority of Chinese Patent Application No. 202410268859.4 filed with the China National Intellectual Property Administration on Mar. 11, 2024, the disclosure of which is incorporated by reference herein in its entirety as part of the present application.

TECHNICAL FIELD

The present disclosure relates to the technical field of the detection of carbon emission gases from farmland, and in particular to an in-situ detection device and method for carbon emissions from farmland.

BACKGROUND

In order to cope with global warming and achieve the goal of carbon neutrality as soon as possible, more attention should be paid to the carbon emissions from agricultural production. At present, the conventional method for collecting carbon emission gas from farmland is basically as follows: putting a collection box with a static state above the plant, sealing the plant area, enriching the gas for a certain period, and then taking the gas in the collection box back to the laboratory for analysis.

However, there is the problem that continuous observation cannot be carried out in the above conventional method of the static box. Meanwhile, the use of the static box will interfere with the measured surface; the temperature, air pressure, humidity, light intensity and gas mixing degree inside the box are different from the natural state outside the box, making it impossible to simulate the natural flow of air on the soil surface. When the crops are closed in the static box for a long time, the photosynthesis and growth of crops will be affected, eventually leading to the deviation between the gas collection result and the actual situation.

Moreover, as most of the sampling is done manually, the nonstandard operation process of the workers will affect the accuracy of the observation result. In general, the gas samples extracted from the box are stored in vacuum glass bottles or gas bags, and the long storage time of the samples will also cause variations in the gas concentration. In addition, when the crops grow to a certain height and reach to a certain density among themselves, the workers are difficult to enter the depths of the farmland to place the enrichment box and collect the gas sample.

SUMMARY

The present disclosure intends to provide an in-situ detection device and method of carbon emissions from farmland, thus solving the problems in the prior art. Under the condition of zero impact and zero damage to crops, the in-situ rapid detection of the carbon emission gas at any position of the farmland is achieved, and the whole unmanned standardized operation is completed, with high detection accuracy and convenient use.

To achieve the intentions above, the present disclosure employs the following technical solutions:

The present disclosure provides an in-situ detection device for carbon emissions from farmland, including an unmanned aerial vehicle and a landing gear. A retraction and release mechanism is arranged between the unmanned aerial vehicle and the landing gear, and the retraction and release mechanism is configured for retracting or lowering the landing gear. An enrichment hood is installed on the landing gear through a folding mechanism, and the folding mechanism can drive the enrichment hood to be unfolded or folded on the landing gear. When the unmanned aerial vehicle lowers the landing gear to a farmland gas collection point through the retraction and release mechanism, the enrichment hood is unfolded to enrich a gas at the farmland gas collection point. The landing gear is also equipped with a greenhouse gas detection mechanism, which is configured to detect the gas enriched in the enrichment hood.

In some embodiments, the landing gear includes two transverse columns. The two transverse columns are horizontally arranged side by side, and a vertical bracket is positioned between the two transverse columns. The folding mechanism includes a rotating bracket, and a drive part. The vertical bracket and the rotating bracket are both of an arch structure. The vertical bracket has two ends fixed to middle parts of the two transverse columns, respectively, and an arch top of the vertical bracket is connected to a bottom of the unmanned aerial vehicle through the retraction and release mechanism. The rotating bracket has two ends that are rotatably connected to the middle parts of the two transverse columns, respectively. The enrichment hood is supported on the vertical bracket and the rotating bracket, and the drive part is configured to drive the rotating bracket to rotate, thus driving the enrichment hood to be unfolded or folded. At least two groups of rotating brackets are provided, and the two groups of rotating brackets are arranged on two sides of the vertical bracket, respectively.

In some embodiments, one end of the rotating bracket is a driving end, and an other end of the rotating bracket is a driven end. The drive part includes a servo motor and a rotating shaft. The servo motor is arranged at a position, close to the driving end of the rotating bracket, on the landing gear, and an output end of the servo motor is connected to the driving end of the rotating bracket through the rotating shaft.

The retraction and release mechanism in some embodiments includes a retraction motor and a hanging rope. The retraction and release motor is arranged at the bottom of the unmanned aerial vehicle, one end of the hanging rope is connected to an output end of the retraction and release motor, and an other end of the hanging rope is connected to the arch top of the vertical bracket.

In some embodiments, the greenhouse gas detection mechanism is arranged at the arch top of the vertical bracket, and the greenhouse gas detection mechanism includes an exhaust pipe, a gas extracting pump and a greenhouse gas detection sensor which are in sequential communication. A gas inlet of the exhaust pipe is in communication with the enrichment hood, and the gas extracting pump is configured for pumping gas in the enrichment hood into the greenhouse gas detection sensor, thus detecting the gas in the enrichment hood.

In some embodiments, the unmanned aerial vehicle is a multi-rotor unmanned aerial vehicle.

In some embodiments, the enrichment hood is a plastic film.

The present disclosure further provides an in-situ detection method for carbon emissions from farmland. The in-situ detection device for carbon emissions from farmland is adopted, and the method includes the following steps:

Step one: uploading position coordinates of a farmland gas collection point to an unmanned aerial vehicle, and making a flight plan for the unmanned aerial vehicle;

Step two: enabling the unmanned aerial vehicle to take off and fly to the farmland gas collection point, lowering a landing gear through a retraction and release mechanism, unfolding an enrichment hood through a folding mechanism, and enriching a gas at the farmland gas collection point through the enrichment hood;

Step three: after reaching a required enrichment time, detecting the gas enriched in the enrichment hood through a greenhouse gas detection mechanism;

Step four: after finishing the detection, folding the enrichment hood through the folding mechanism, and retracting the landing gear through the retraction and release mechanism; and Step five, enabling the unmanned aerial vehicle to return or fly to a next farmland gas collection point, and repeatedly carrying out the Step two to Step four.

Compared with the prior art, the present disclosure has the following technical effects:

The in-situ detection device for carbon emissions from the farmland includes an unmanned aerial vehicle, and a landing gear. A retraction and release mechanism is arranged between the unmanned aerial vehicle and the landing gear, and an enrichment hood is installed on the landing gear through a folding mechanism. During use, the unmanned aerial vehicle hovers over a farmland gas collection point, the landing gear is lowered by the retraction and release mechanism, and the folding mechanism unfolds the enrichment hood. The gas in the farmland gas collection point is enriched by the enrichment hood. When the required enrichment time is reached, a greenhouse gas detection mechanism detects the gas enriched in the enrichment hood. After finishing the detection, the enrichment hood is folded by the folding mechanism, the landing gear is retracted by the retraction and release mechanism, and the unmanned aerial vehicle can return or fly to the next farmland gas collection point. Under the condition of zero impact and zero damage to crops, the in-situ rapid detection of the carbon emission gas at any position of the farmland is achieved, and the whole unmanned standardized operation is completed, with high detection accuracy and convenient use.

BRIEF DESCRIPTION OF THE DRAWINGS

To describe the technical solutions of the embodiments of the present disclosure or in the prior art more clearly, the following briefly introduces the accompanying drawings required in the embodiments. Apparently, the accompanying drawings in the following description show merely some embodiments of the present disclosure, and those skilled in the art may still derive other drawings following these accompanying drawings without creative efforts.

Figure 1:
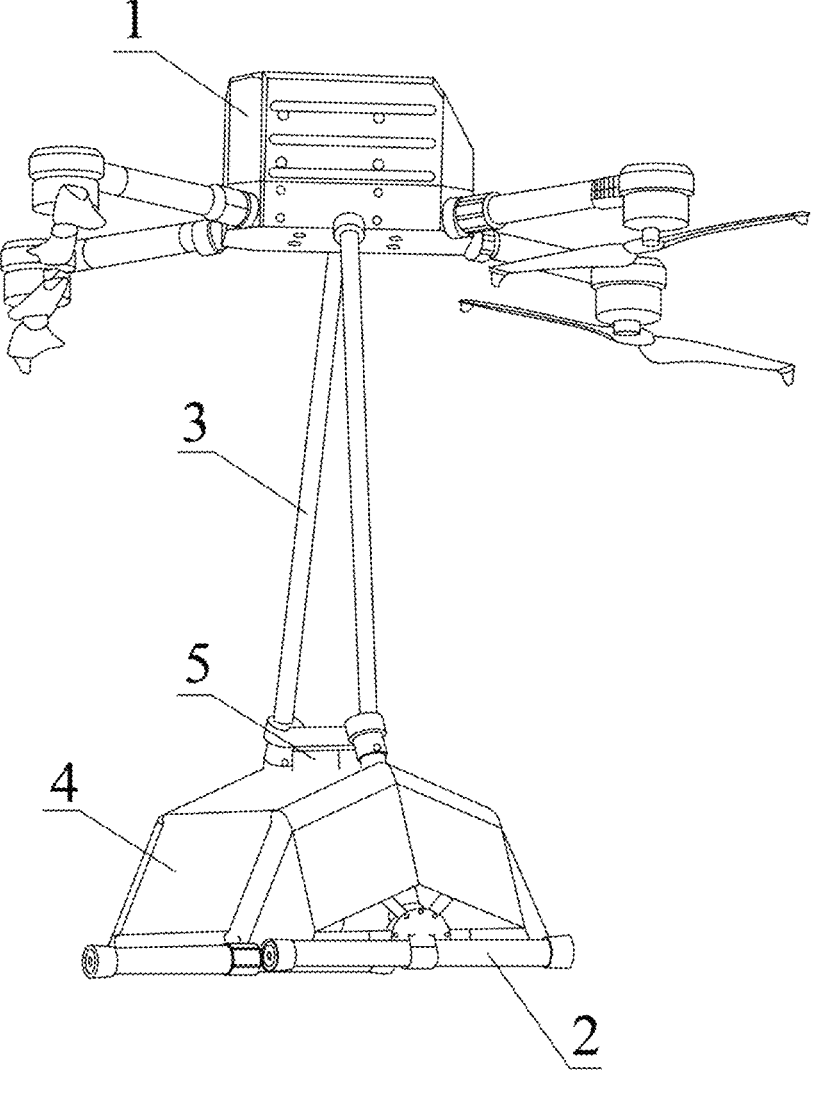
FIG. 1 is a schematic diagram of an in-situ detection device of carbon emissions from farmland according to Embodiment I of the present disclosure in an enrichment condition.

In the drawings: 1—unmanned aerial vehicle; 2—landing gear; 201—transverse column; 202—vertical bracket; 203—rotating bracket; 204—drive part; 3—retraction and release mechanism; 4—enrichment hood; 5—greenhouse gas detection mechanism.

DETAILED DESCRIPTION OF THE EMBODIMENTS

The following clearly and completely describes the technical solutions in the embodiments of the present disclosure concerning the accompanying drawings in the embodiments of the present disclosure. Apparently, the described embodiments are merely a part rather than all of the embodiments of the present disclosure. All other embodiments obtained by those skilled in the art based on the embodiments of the present disclosure without creative efforts shall fall within the scope of protection of the present disclosure.

The present disclosure intends to provide an in-situ detection device and method of carbon emissions from farmland, thus solving the problems in the prior art. Under the condition of zero impact and zero damage to crops, the in-situ rapid detection of the carbon emission gas at any position of the farmland is achieved, and the whole unmanned standardized operation is completed, with high detection accuracy and convenient use.

In order to make the intentions, features and advantages of the present disclosure more clear, the present disclosure is further described in detail below concerning the accompanying drawings and specific implementations.

Embodiment I

Figure 2:
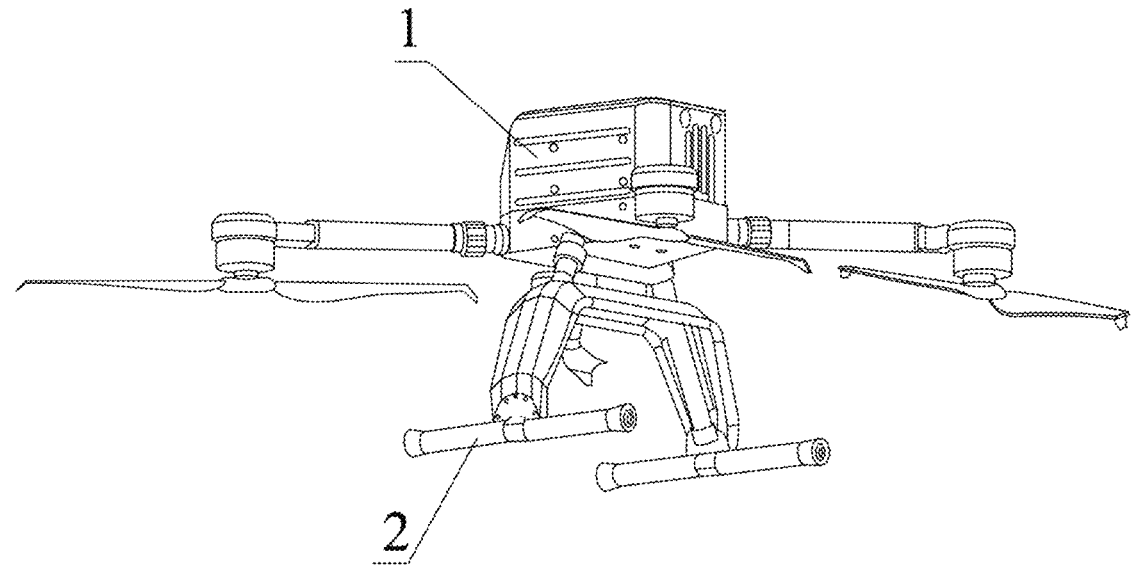
FIG. 2 is a schematic diagram of an in-situ detection device of carbon emissions from farmland according to Embodiment I of the present disclosure in a retraction state of a landing gear.

As shown in FIG. 1 to FIG. 2, an in-situ detection device for carbon emissions from farmland is provided in this embodiment, including an unmanned aerial vehicle 1, and a landing gear 2. In this embodiment, the unmanned aerial vehicle 1 is preferably a multi-rotor unmanned aerial vehicle. A retraction and release mechanism 3 is arranged between the unmanned aerial vehicle 1 and the landing gear 2, and the retraction and release mechanism 3 is configured for retracting or lowering the landing gear 2. An enrichment hood 4 is installed on the landing gear 2 through a folding mechanism, and the folding mechanism can drive the enrichment hood 4 to be unfolded or folded on the landing gear 2. When the unmanned aerial vehicle 1 lowers the landing gear 2 to a farmland gas collection point through the retraction and release mechanism 3, the enrichment hood 4 is unfolded to enrich a gas at the farmland gas collection point. The landing gear 2 also provides a greenhouse gas detection mechanism 5 for detecting the gas enriched in the enrichment hood 4. Under the condition of zero impact and zero damage to crops, the in-situ rapid detection of the carbon emission gas at any position of the farmland is achieved, and the whole unmanned standardized operation is completed, with high detection accuracy and convenient use.

Figure 3:
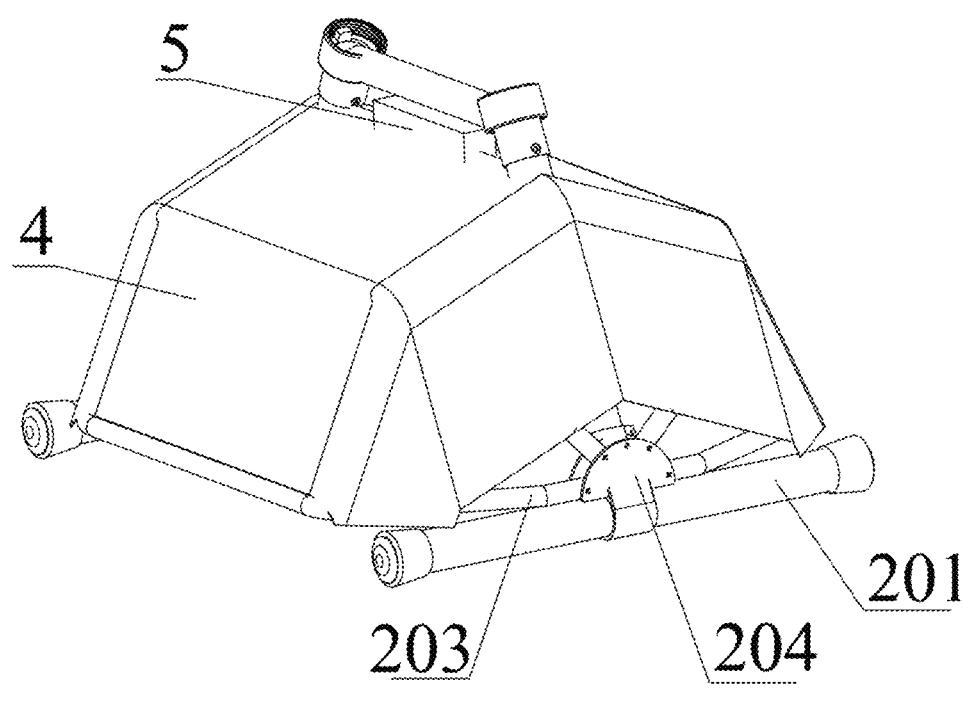
FIG. 3 is a schematic diagram of a first angle of a landing gear according to Embodiment I of the present disclosure.
Figure 4:
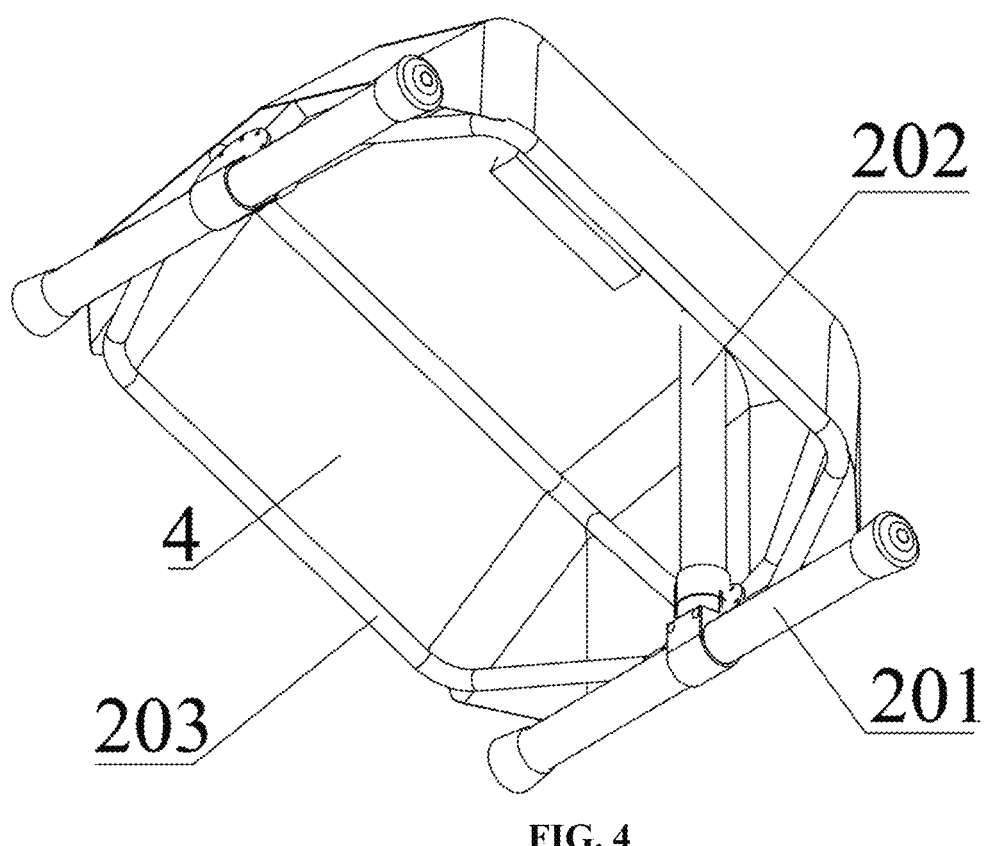
FIG. 4 is a schematic diagram of a second angle of a landing gear according to Embodiment I of the present disclosure.

In this embodiment, as shown in FIG. 3 and FIG. 4, the landing gear 2 includes two transverse columns 201. The two transverse columns 201 are horizontally arranged side by side, and a vertical bracket 202 is positioned between the two transverse columns 201. The folding mechanism includes a rotating bracket 203, and a drive part 204. The vertical bracket 202 and the rotating bracket 203 are both of an arch structure. Both ends of the vertical bracket 202 are fixed to the middle parts of the two transverse columns 201, respectively, and an arch top of the vertical bracket 202 is connected to the bottom of the unmanned aerial vehicle 1 through the retraction and release mechanism 3. Both ends of the rotating bracket 203 are rotatably connected to the middle parts of the two transverse columns 201, respectively. The enrichment hood 4 is supported on the vertical bracket 202 and the rotating bracket 203, and the drive part 204 is configured to drive the rotating bracket 203 to rotate, thus driving the enrichment hood 4 to be unfolded or folded. At least two groups of rotating brackets 203 are provided, and the two groups of rotating brackets 203 are arranged on both sides of the vertical bracket 202, respectively. Specifically, in this embodiment, there are four groups of rotating brackets 203, two groups of the four groups of rotating brackets 203 are located on the front side of the vertical bracket 202, and the other two groups of the four groups of rotating brackets 203 are located on a rear side of the vertical bracket 202. In some embodiments, the enrichment hood 4 is a plastic film, the plastic film covers the four groups of rotating brackets 203 from front to back, and the middle part of the plastic film is fixed to the vertical bracket 202 and is located at the highest position of the landing gear 2.

In some embodiments, one end of the rotating bracket 203 is a driving end, and the other end of the rotating bracket 203 is a driven end. The drive part 204 includes a servo motor, and a rotating shaft. The servo motor is arranged at a position, close to the driving end of the rotating bracket 203, on the landing gear 2, and an output end of the servo motor is connected to the driving end of the rotating bracket 203 through the rotating shaft. During use, the servo motor drives the rotating shaft to rotate, thus driving each rotating bracket group to rotate. When the first group of rotating brackets 203 and the last group of rotating brackets 203 are rotated to be nearly parallel to the transverse column 201, the enrichment hood 4 is in an unfolded state, and can achieve the carbon emission gas enrichment function at the farmland gas collection point. When each group of rotating brackets 203 rotates to be nearly parallel to the vertical brackets 202, the enrichment hood 4 is in a folded state, which does not affect the normal flight of the unmanned aerial vehicle 1.

In this embodiment, the retraction and release mechanism 3 includes a retraction and release motor, and a hanging rope. The retraction and release motor is arranged at the bottom of the unmanned aerial vehicle 1. One end of the hanging rope is connected to an output end of the retraction and release motor, and the other is connected to the arch top of the vertical bracket 202. The hanging rope hangs the landing gear 2. During use, the rope is retracted or released through the retraction and release motor, thus achieving the retraction/lowering of the landing gear 2.

In this embodiment, the greenhouse gas detection mechanism 5 is arranged at the arch top of the vertical bracket 202, and includes an exhaust pipe, a gas extracting pump and a greenhouse gas detection sensor which are in sequential communication. A gas inlet of the exhaust pipe is communicated with the enrichment hood 4, and the gas extracting pump is configured to pump the gas in the enrichment hood 4 into the greenhouse gas detection sensor to detect the gas in the enrichment hood 4. It should be noted that the greenhouse gas detection sensor can detect the concentration of a greenhouse gas such as carbon dioxide, and record the detection data. The temperature gas detection sensor is an existing mature technology, and can be selected as required by those skilled in the art.

Embodiment II

An in-situ detection method for carbon emissions from farmland is provided in this embodiment, in which the above-mentioned in-situ detection device for carbon emissions from farmland is adopted, and the method includes the following steps:

Step one, the position coordinates of a farmland gas collection point are uploaded to an unmanned aerial vehicle 1, and a flight plan for the unmanned aerial vehicle is made.

Step two, the unmanned aerial vehicle 1 takes off and flies to the farmland gas collection point, the landing gear 2 is lowered through a retraction and release mechanism 3, an enrichment hood 4 is unfolded through a folding mechanism, and the gas at the farmland gas collection point is enriched through the enrichment hood 4.

Step three, after reaching the required enrichment time, the gas enriched in the enrichment hood 4 is detected through a greenhouse gas detection mechanism 5.

Step four, after finishing the detection, the enrichment hood 4 is folded through the folding mechanism, and the landing gear 2 is retracted through the retraction and release mechanism 3.

Step five, the unmanned aerial vehicle 1 returns or flies to the next farmland gas collection point, and steps two to four are repeated.

In conclusion, the in-situ detection device and method for carbon emissions from farmland provided by the present disclosure have the following advantages:

First, the present disclosure can improve the traditional detection method for the carbon emission gas from farmland, improve the timeliness and continuity of the detection of the carbon emissions from farmland, and achieve real-time monitoring of greenhouse gas emissions during crop growth.

Second, according to the present disclosure, the repeatability detection accuracy for the same carbon emission gas detection point of the farmland is improved, and long-term observation of the same geographical coordinate point can be achieved. By collecting greenhouse gas emission data of the farmland with high temporal and spatial resolution, better theoretical support is provided for a carbon emission model, which is conducive to reducing the uncertainty in predicting future carbon emissions from the farmland.

Third, according to the present disclosure, the influence of conventional detection methods on crops is eliminated, the problem of damaging crops due to the entry of people or machinery into farmland is solved, and meanwhile, the labor intensity of workers is greatly reduced.

Specific examples are used herein to illustrate the principles and implementations of the present disclosure. The description of the above embodiments is merely used to help understand the method and its core principles of the present disclosure. In addition, those skilled in the art can make various modifications in terms of specific implementations and application scope in accordance with the teachings of the present disclosure. In conclusion, the content of this specification shall not be construed as a limitation to the present disclosure.

7

8

What is claimed is:

1. An in-situ detection device for carbon emissions from farmland, comprising:

an unmanned aerial vehicle;

a landing gear having an enrichment hood installed on the landing gear through a folding mechanism and a greenhouse gas detection system, the folding mechanism being capable of driving the enrichment hood to be unfolded or folded on the landing gear, and the greenhouse gas detection mechanism is configured to detect gas enriched in the enrichment hood; and a retraction and release mechanism arranged between the unmanned aerial vehicle and the landing gear, the retraction and release mechanism retracts or lowers the landing gear;

wherein when the unmanned aerial vehicle lowers the landing gear to a farmland gas collection point through the retraction and release mechanism, the enrichment hood is unfolded to enrich a gas at the farmland gas collection point.

2. The in-situ detection device for carbon emissions from farmland according to claim 1, wherein the landing gear further comprises:

two transverse columns horizontally arranged side by side, and a vertical bracket arranged between the two transverse columns and having two ends which are fixed to middle parts of the two transvers columns, respectively;

the folding mechanism further comprises:

at least two groups of rotating brackets each having two ends rotatably connected to the middle parts of the two transverse columns, respectively, the vertical bracket and each group of the rotating brackets are both of an arch structure and a top of the arch structure of the vertical bracket is connected to a bottom of the unmanned aerial vehicle through the retraction and release mechanism; and a drive part configured to drive the rotating bracket to rotate, the enrichment hood being supported on the vertical bracket and the rotating bracket, and the drive part via the rotating bracket drives the enrichment hood to be unfolded or folded;

wherein the at least two groups of rotating brackets are arranged on two sides of the vertical bracket, respectively.

3. The in-situ detection device for carbon emissions from farmland according to claim 2, wherein one end of the rotating bracket is a driving end, and an other end of the rotating bracket is a driven end;

the drive part further comprises a servo motor and a rotating shaft, the servo motor is arranged at a position, close to the driving end of the rotating bracket, on the landing gear, and an output end of the servo motor is connected to the driving end of the rotating bracket through the rotating shaft.

4. The in-situ detection device for carbon emissions from farmland according to claim 3, wherein the enrichment hood is a plastic film.

5. The in-situ detection device for carbon emissions from farmland according to claim 2, wherein the retraction and release mechanism further comprises a retraction and release motor arranged at the bottom of the unmanned aerial vehicle and a hanging rope having one end connected to an output end of the retraction and release motor, and an other end connected to the arch top of the vertical bracket.

6. The in-situ detection device for carbon emissions from farmland according to claim 5, wherein the enrichment hood is a plastic film.

7. The in-situ detection device for carbon emissions from farmland according to claim 2, wherein the greenhouse gas detection mechanism is arranged at the arch top of the vertical bracket, and the greenhouse gas detection mechanism comprises an exhaust pipe, a gas extracting pump and a greenhouse gas detection sensor which are in sequential communication, a gas inlet of the exhaust pipe is in communication with the enrichment hood, and the gas extracting pump is configured to pump gas in the enrichment hood into the greenhouse gas detection sensor, thus detecting the gas in the enrichment hood.

8. The in-situ detection device for carbon emissions from farmland according to claim 7, wherein the enrichment hood is a plastic film.

9. The in-situ detection device for carbon emissions from farmland according to claim 2, wherein the enrichment hood is a plastic film.

10. The in-situ detection device for carbon emissions from farmland according to claim 1, wherein the unmanned aerial vehicle is a multi-rotor unmanned aerial vehicle.

11. The in-situ detection device for carbon emissions from farmland according to claim 10, wherein the enrichment hood is a plastic film.

12. The in-situ detection device for carbon emissions from farmland according to claim 1, wherein the enrichment hood is a plastic film.

13. An in-situ detection method for carbon emissions from farmland, wherein the in-situ detection device for carbon emissions from farmland according to claim 1 is adopted, and the method comprises:

uploading position coordinates of a farmland gas collection point to an unmanned aerial vehicle, and making a flight plan for the unmanned aerial vehicle;

enabling the unmanned aerial vehicle to take off and fly to the farmland gas collection point, lowering a landing gear through a retraction and release mechanism, unfolding an enrichment hood through a folding mechanism, and enriching a gas at the farmland gas collection point through the enrichment hood;

after reaching a required enrichment time, detecting the gas enriched in the enrichment hood through a greenhouse gas detection mechanism;

after finishing the detection, folding the enrichment hood through the folding mechanism, and retracting the landing gear through the retraction and release mechanism; and enabling the unmanned aerial vehicle to return or fly to a next farmland gas collection point, and repeatedly carrying out the steps two to four.

* * * * *